United States Patent [19]

Schweitzer et al.

[11] Patent Number: 4,580,567

[45] Date of Patent: Apr. 8, 1986

[54] SUTURE NEEDLE HOLDER

[75] Inventors: Eugene J. Schweitzer, Moonachie, N.J.; James R. Bresch, Gaithersburg, Md.

[73] Assignee: The United States of America as represented by the Secretary of the Army, Washington, D.C.

[21] Appl. No.: 740,610

[22] Filed: Jun. 3, 1985

[51] Int. Cl.⁴ .............................................. A61B 17/06
[52] U.S. Cl. .................................. 128/340; 128/321; 112/80
[58] Field of Search ............... 128/339, 340, 321, 322; 112/80

[56] References Cited

U.S. PATENT DOCUMENTS

| | | | |
|---|---|---|---|
| 3,807,407 | 4/1974 | Schweizer | 128/334 R |
| 3,842,840 | 10/1974 | Schweizer | 128/334 R |
| 4,011,870 | 3/1977 | Goldstein | 128/276 |
| 4,135,506 | 1/1979 | Ulrich | 128/92 B |
| 4,165,745 | 8/1979 | Heifetz | 128/318 |
| 4,287,890 | 9/1981 | Fogarty | 128/303 R |
| 4,446,866 | 5/1984 | Davison | 128/340 |

Primary Examiner—Richard C. Pinkham
Assistant Examiner—Gary Jackson
Attorney, Agent, or Firm—John H. Raubitschek; Francis A. Cooch; Werten F. W. Bellamy

[57] ABSTRACT

A typical embodiment of the invention enables a surgeon to occupy only one hand in manipulating a suture needle. The instrument thumb handle has, on one end, a freely rotatable short roller. The ring finger handle, moreover, has a long roller that is journalled within that handle. One end of the long roller bears against the short roller to form a nip that engages the suture needle. The other end of the long roller terminates near the ring finger handle grip to enable the surgeon to rotate the long roller with another finger of the same hand and thereby draw the needle through the nip, repositioning the needle for another stitch.

4 Claims, 4 Drawing Figures

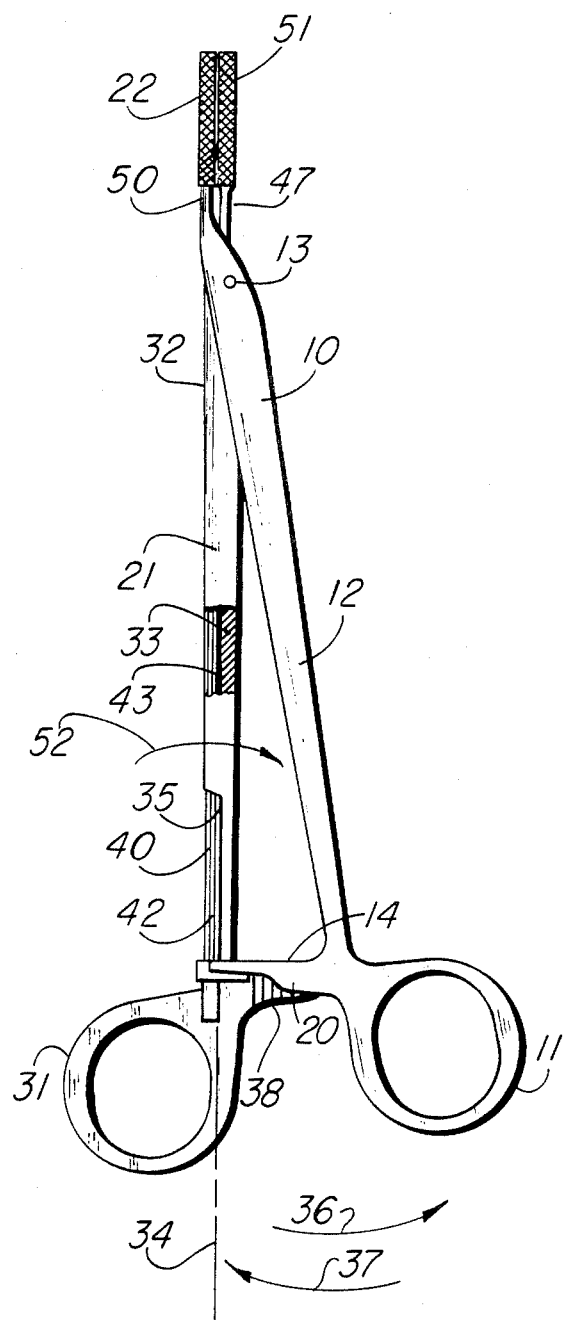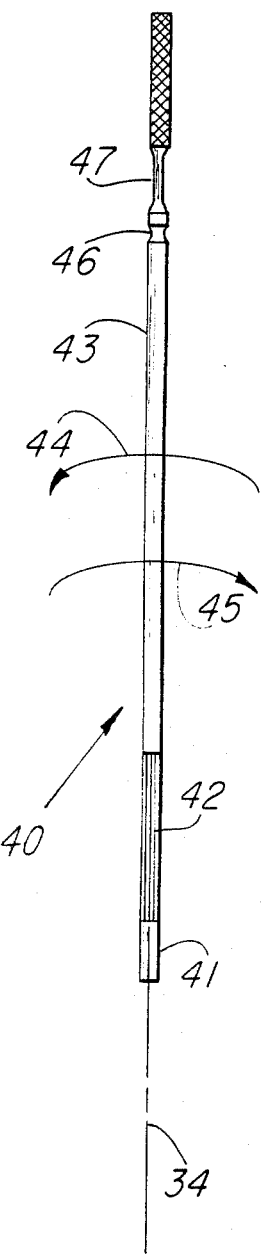
FIG. 1
FIG. 2

SUTURE NEEDLE HOLDER

BACKGROUND OF THE INVENTION

This invention relates to surgical apparatus and, more particularly, to a suture needle holder that has rollers to grasp the needle tip to rotate the needle into position for the next stitch, and the like.

Suturing incisions and wounds is a demanding surgical skill. As practiced, a curved suture needle is mounted in a simple holder that is held in the surgeon's right hand. To complete a stitch, frequently the needle is grasped with forceps that are held in the surgeon's left hand and tip of the needle is released from the needle holder. The holder then grasps the back end of the suture needle in order to press the needle through and complete the stitch.

Clearly, this technique requires the surgeon to use both hands in order to suture a wound or incision. The manipulations are cumbersome, tedious and time consuming. Unquestionably, there is a need for some technique that would not require the surgeon to use both hands to complete a single stitch and that would take less time and physical stress.

SUMMARY OF THE INVENTION

The invention provides an apparatus that enables a surgeon to manipulate a suture needle with one hand. More specifically, a short, free-spinning roller is mounted on the end of a handle. A long roller is journalled in the body of a second handle to enable a portion of the long roller to protrude from the end of the handle parallel with and adjacent to the short roller. After the tip of the needle is grasped between the rollers and the needle is removed from the tissue, the needle is rolled forward by rotating a portion of the shank of the long roller that is opposite to the end engaging the needle with the middle finger of the right hand. The needle is thus rolled forward until it is held by both rollers near the end that receives the suture.

Held in the foregoing manner, the needle now is poised for introduction into the patient for the next stitch. During these manipulations the surgeon's left hand remains free for other purposes.

Thus, there is provided an improved suturing apparatus. For a more complete appreciation of the invention, attention is invited to the following detailed description of a preferred embodiment, taken with the drawing. The scope of the invention, however, is limited only through the claims.

BRIEF DESCRIPTION OF THE DRAWING

FIG. 1 of the drawing is a plan view of a typical embodiment of the invention;

FIG. 2 is a plan view of a long roller for use in the apparatus shown in FIG. 1;

DETAILED DESCRIPTION OF A PREFERRED EMBODIMENT

These and other problems that have characterized the prior art are overcome, to a great extent, through the practice of the invention. As shown in FIG. 1, a thumb handle 10 has, on one end, a generally oval thumb grip 11. The thumb grip 11 is attached to an offset, long, slender shank 12 that has, near the end that is opposite to the thumb grip, a transversely disposed fulcrum pin 13.

Figure 4:
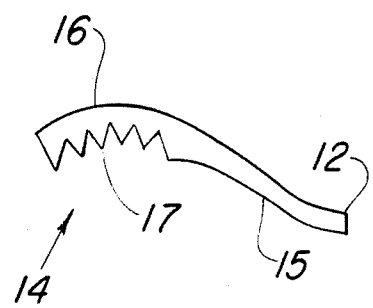
FIG. 4 is a detail view of a roller locking finger for use with the apparatus shown in FIG. 1.

A roller locking finger 14 protrudes from the shank 12 on the side that is opposite to the thumb grip 11 and on that portion of the shank to which the thumb grip is joined. As best shown in FIG. 4, the locking finger 14 is a resilient, arcuate beam 15 that is cantilevered from the shank 12. Free end 16 of the beam 15 has in its inner curved surface, a number of teeth 17, the lengthwise axes of which are parallel with the major axis of the shank 12 shown in FIG. 1.

A locking cam 20 also is formed integrally with the roller locking finger. The cam 20 has the usual meshing cam surface (not shown in the drawing) to clamp the thumb handle 10 to a ring finger handle 21 which is joined to the thumb handle by means of the fulcrum pin 13.

Figure 3:
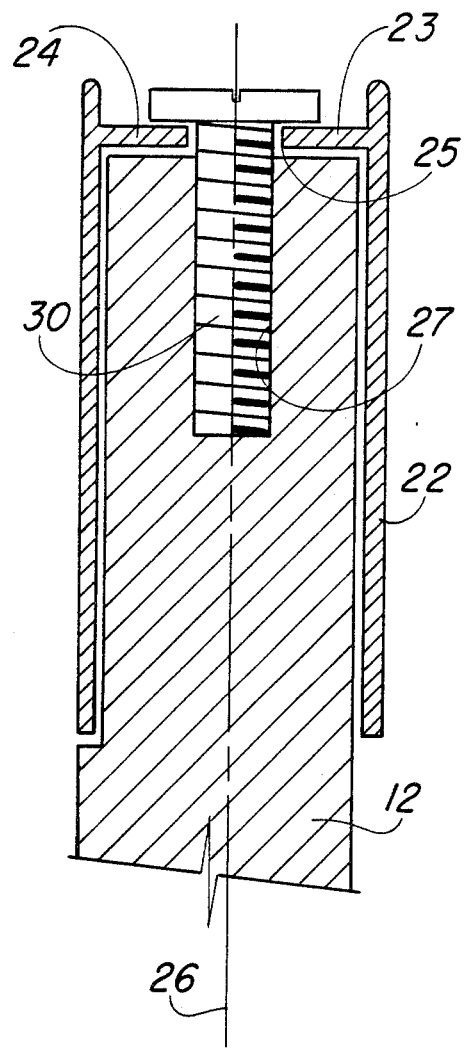
FIG. 3 is a plan view in full section of a short roller attached to the apparatus of FIG. 1.

Continuing with the description of the thumb handle 10, the end of the shank 12 that is opposite to the thumb grip 11 terminates in a short roller 22. As illustrated, the short roller 22 is generally cylindrical, the outer surface of the cylinder being finished by knurling, or some other suitable gripping surface that enjoys an high coefficient of friction. Turning for the moment to FIG. 3, it can be seen that the short roller 22 is an hollow cylinder, open on the end that is oriented toward the thumb grip 11 (not shown in FIG. 3) in order to telescope over the associated end portion of the shank 12. Opposite end 23 of the short roller 22 terminates in a transverse partition 24 that has a centrally disposed bore 25. The bore 25 is in general alignment with longitudinal axis 26 of the shank 12. A tapped bore 27, moreover, is formed in the end of the shank 12. The tapped bore 27 also is in longitudinal alignment with the axis 26 in order to receive a threaded pivot screw 30 that joins the short roller 22 to the shank 12. In this way the short roller 22 is free to rotate in a clockwise or counterclockwise direction relative to the longitudinal axis 26.

In FIG. 1, the ring finger handle 21 has, at one extreme end a generally oval ring finger grip 31 that is in the same plane as the thumb grip 11, but is offset in the opposite direction to the thumb grip. The shank 32 has a lengthwise journal bearing 33 that is in general alignment with longitudinal axis 34 of the ring finger handle 21.

In accordance with a salient feature of the invention, a bight 35 is formed in the shank to expose an end of the journal bearing 33 that is adjacent to the ring finger grip 31. A ring finger handle locking cam 38 protrudes from the shank 32 at the junction between the shank and the ring finger grip 31. As shown, the locking cam 38 extends toward and aligns with the corresponding locking cam 20 on the thumb handle 10 in order to selectively mate with the cam surfaces (not shown in the drawing) on the cam 20 and thereby to fix the relative positions of the handles 10,21.

Near the tip of the ring finger handle 21 that is opposite to the bight 35 a portion of the fulcrum pin 13 is secured in the handle to restrict the handles 10,21 to a scissors-like motion in the plane of the grips 11,31 and in the directions of arrows 36,37.

A long roller 40 is mounted in the journal bearing 33 in accordance with a further salient feature of the invention. The long roller 40 is in general longitudinal alignment with the axis 34 within the bearing 33 and is, perhaps, best shown in FIG. 2. Thus, the long roller 40 has, at one end, a short bearing stub 41 that has a smoothly machined surface. Spaced immediately inward of the stub 41 is an array of short, lengthwise teeth 42. In accordance with the invention the long roller teeth 42 have the same pitch and depth as the teeth 17 (FIG. 4) on the arcuate beam 15 in order to mesh selectively with the teeth on the beam.

Turning once more to FIG. 2, the long roller 40 has a smoothly finished central portion 43 in order to rotate freely in the journal bearing 33 (FIG. 1) in which the long roller is mounted. This rotation, relative to the longitudinal axis 34, is in the directions of arrows 44,45.

Near the end of the long roller 40 that is opposite to the stub 41, a circumferential groove 46 is formed to serve two main purposes. Thus, the groove not only provides a clearance for the fulcrum pin 13 (FIG. 1), but also enables the fulcrum pin to act as a stop, thereby retaining the long roller within the ring finger handle 21 and preventing the long roller from slipping out of the shank 32 during use.

Between the fulcrum groove 46 and the extreme end of the long roller 40 a further circumferential groove 47 is formed to establish a clearance between the long roller and a terminal, angled portion 50 of the thumb handle 10.

The end portion of the long roller 40, moreover, terminates in a cylindrical surface 51 that has a knurled, or other suitable highfriction finish to provide a firm grip for the purpose of the invention.

In operation, the surgeon inserts thumb and ring fingers in the respective grips 11,31 and squeezes the handles 10,21 together in the direction of the arrow 37 in order to disengage the roller locking finger 14 from the ring finger locking cam 38 and to unmesh the locking cams 20,38. The handles 10,21 are then spread apart by pressing the thumb grip 11 in the direction of the arrow 36 and the ring finger grip 31 in the direction of the arrow 37. The handles 10,21 thus are compelled to pivot about the fulcrum pin 13 and thereby spread the rollers 22,40 apart.

The tip of a suture needle (not shown in the drawing) is placed between the knurled surfaces of the short roller 22 and the cylindrical surface 51 of the long roller 40. After so positioning the suture needle tip between the rollers 22,40, the thumb grip 11 is pivoted in the direction of the arrow 37 and the ring finger grip 31 is pivoted in the direction of the arrow 36 in order to grasp the tip of the suture needle between the knurled surfaces of the rollers 22,40.

Upon so clamping the tip of the needle between the rollers 22,40, the locking cams 20,38 on the handles 10,21, respectively, are engaged in order to engage the needle between the rollers without requiring any further physical effort or attention on the part of the surgeon. The surgeon then removes the needle from the tissue.

At this point, and in accordance with one of the principles of the invention, after the needle is free from the patient's tissue, the surgeon presses the middle finger of the same hand used to manipulate the thumb and ring finger grips 11,31 against the teeth 42 on the long roller 40 that are exposed in the bight 35. The middle finger then bears against the long roller 40 to compel the roller to rotate in the direction of arrow 52 relative to the longitudinal axis 34. This rotation, transmitted by way of the journalled center portion 43 of the long roller 40, causes the knurled cylindrical surface 51 also to rotate in the same direction as the arrow 52. Friction forces imposed by the knurled roller surfaces and the rotational motion of the surface 51 in the direction of the arrow 52 and, reactively, the movement of the freely rotating short roller 22 in the opposite direction, force the suture needle (not shown in the drawing) to advance through the nip of the rollers in a direction that is perpendicular to the plane of the thumb grips 11,31 toward the viewer.

The needle is advanced between the rollers 22,40 until the back end of the needle, near the suture, is reached. The long roller locking finger 14 is then meshed with the teeth 42 on the long roller 40 in order to stop temporarily the rotation of the long roller and the companion short roller 22 until the surgeon is prepared to release the back of the needle and to reengage the needle tips.

From this position, with the back of the needle gripped in the nip of the rollers 22,40, the needle can be reintroduced into the tissue for the next stitch. All of these manipulations, moreover, are carried out in a manner that requires the surgeon to use only one hand to complete the necessary suturing steps. In this way, the surgeon has a free hand to press the sides of the incision together or for other surgical purposes as the circumstances may dictate.

I claim:

1. An instrument for manipulating a suture and suture needle comprising, a thumb handle, a thumb grip on one end of said handle, a short roller secured to the opposite end of said handle and freely rotatable relative to the axis of said handle, a ring finger handle pivotally jointed to said thumb handle having a lengthwise journal formed therein and having a bight formed near one end of said handle to expose a portion of said journal, a ring finger grip on the end of said ring finger handle that is closest to said bight, a long roller received in said journal for rotation relative thereto, one end of said long roller exposed in said ring finger handle bight and the other end of said long roller protruding from the opposite end of said ring finger handle to selectively bear against said short roller and to form a nip therewith, and a fulcrum for pivotally joining said thumb and ring finger handles together to clasp the suture needle in said nip and to advance the needle through said nip.

2. An instrument according to claim 1 further comprising a plurality of lengthwise oriented teeth formed in said long roller exposed within said bight to promote rotation of said long roller, and a roller locking finger protruding from said thumb handle in alignment with said bight and said exposed long roller teeth, said roller locking finger having teeth formed thereon to mesh selectively with said long roller teeth.

3. An instrument according to claim 1 wherein said short roller and said protruding long roller end each further comprise knurled surfaces.

4. An instrument according to claim 1 further comprising a locking cam protruding from said thumb handle toward said ring finger handle and another locking cam protruding from said ring finger handle toward said thumb handle to selectively mesh together and to prevent said handles from moving relative to each other.

* * * * *